United States Patent [19]

Bayerlein

[11] Patent Number: 4,917,080

[45] Date of Patent: Apr. 17, 1990

[54] METHOD FOR CONTROLLING A VENTILATING APPARATUS USING A SIMULATOR ARRANGEMENT

[75] Inventor: Jörg Bayerlein, Stockelsdorf, Fed. Rep. of Germany

[73] Assignee: Drägerwerk Aktiengesellschaft, Lübeck, Fed. Rep. of Germany

[21] Appl. No.: 354,030

[22] Filed: May 19, 1989

[30] Foreign Application Priority Data

May 19, 1988 [DE] Fed. Rep. of Germany ....... 3817053

[51] Int. Cl.⁴ ............................................. A61M 16/00
[52] U.S. Cl. ................................ 128/204.23; 128/716; 73/195
[58] Field of Search ...................... 128/204.21, 204.23, 128/204.26, 671, 716, 718, 719, 720, 721, 722, 724, 725–730; 73/23, 195

[56] References Cited

U.S. PATENT DOCUMENTS

| | | | |
|---|---|---|---|
| 3,927,670 | 12/1975 | Turney et al. | 128/719 |
| 3,977,394 | 8/1976 | Jones et al. | 128/728 |
| 3,991,304 | 11/1976 | Hillsman | 128/720 |
| 4,034,743 | 7/1977 | Greenwood et al. | 128/725 |
| 4,211,221 | 7/1980 | Schwanbom et al. | 128/204.26 |
| 4,296,756 | 10/1981 | Dunning et al. | 128/716 |
| 4,326,513 | 4/1982 | Schulz | 128/204.23 |
| 4,444,201 | 4/1984 | Itoh | 128/204.23 |
| 4,475,558 | 10/1984 | Brock | 128/716 |
| 4,686,975 | 8/1987 | Naimon et al. | 128/204.23 |
| 4,796,639 | 1/1989 | Snow et al. | 128/719 |
| 4,798,538 | 1/1989 | Yagi | 128/721 |

*Primary Examiner*—Eugene H. Eickholt
*Attorney, Agent, or Firm*—Walter Ottesen

[57] ABSTRACT

The invention is directed to a method for controlling a ventilating apparatus wherein an adjustment selected according to patient data is changed for optimization after a work-in time period. A first simulator unit simulating the characteristic values of the ventilating apparatus and a second simulator unit simulating patient parameters taken from patient data are connected to a ventilating apparatus such that the new adjustment is processed first on the first simulator unit with unchanged adjustment of the ventilating apparatus. The resulting output values of the first simulator unit are coupled with the patient data of the second simulator unit such that the effects of the changed adjustment on the patient are derived as simulated new patient data. A switchover of the ventilating apparatus to the new adjustment can take palce by means of a control command.

3 Claims, 1 Drawing Sheet

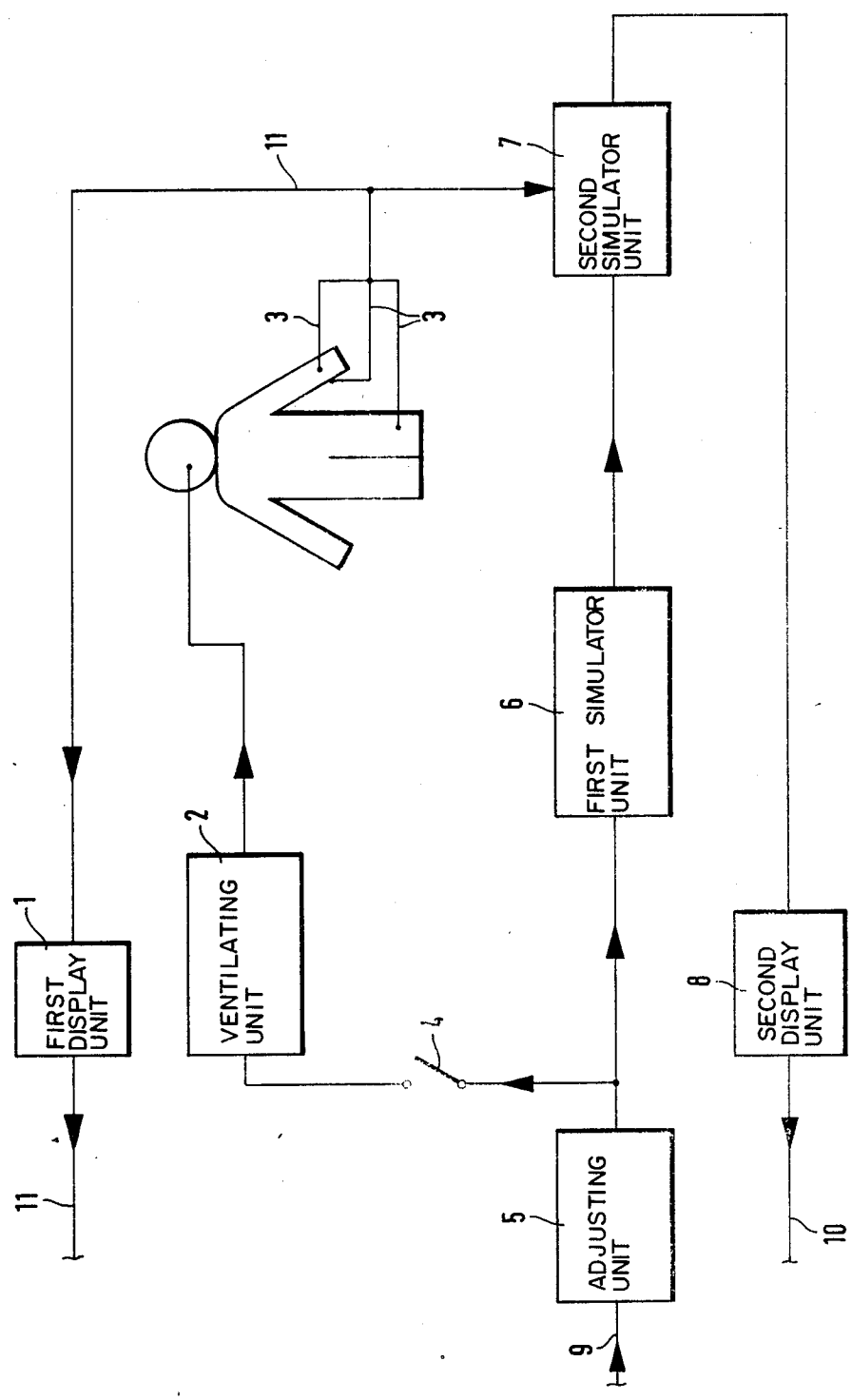

METHOD FOR CONTROLLING A VENTILATING APPARATUS USING A SIMULATOR ARRANGEMENT

FIELD OF THE INVENTION

The invention relates to a method for controlling a ventilating apparatus for which an adjustment selected according to patient data is to be changed for optimization after a work-in time period.

BACKGROUND OF THE INVENTION

When adjusting ventilating apparatus such as in the intensive care of patients, specific adjusting values are first set according to the clinical condition of the patient. Observations are made as to whether an improved physiological overall situation or a stabilization of the breathing system can be obtained with a ventilation with these values. The first adjustment must in many situations be subsequently changed and such changes often lead to unforeseen and sometimes dangerous reactions in the patient. For these reasons, it is desirable to know at least approximately the effects of a new adjustment before a corresponding change in the basic adjustment of the ventilating apparatus is carried out.

An anesthesia simulator is disclosed in the publication "Abbott-Narkosesimulator" by Helmut Schwilden (Deutsche Abbott GmbH, Dec. 1986). In this anesthesia simulator, the possible vaporizer adjustment of the anesthesia apparatus is coupled to parameters of the ventilating system and certain physiological quantities of the patient with the aid of a computer.

After adjusting the patient data essential for the anesthesia and the anesthesia apparatus, the inhalation anesthesia medium is selected and the dosis thereof is fixed. Such a simulation makes possible a selection of the anesthesia medium adapted to the patient and the determination of the dosis required therefor as well as additional ventilating variables. The simulation further permits the display of a time-dependent profile for the course of the anesthesia to be expected. However, this simulation is not carried out during the course of the anesthesia; instead, the simulation serves to determine the adjusting variables to be selected in the later anesthesia process and serves to determine an advantageous selection of the anesthetic medium.

SUMMARY OF THE INVENTION

It is an object of the invention to provide a method of controlling a ventilating apparatus such that an experimental change can be fictitiously carried out during the ventilation and in advance of a change of the selected adjustments which makes possible an estimate with respect to the changed patient data to be expected as a consequence of the changed adjustment.

According to a feature of the invention, a first simulator unit simulating the characteristic values of the ventilating apparatus (model of the ventilating apparatus) and a second simulator unit (patient model) simulating the patient parameters from the patient data are connected with the ventilating apparatus such that the anticipated new adjustment (with the adjustment of the ventilating apparatus unchanged) is first carried out in the first simulator unit so that the resulting output values can be coupled with the patient data of the second simulator unit such that the effect of the changed adjustment on the patient can be derived as simulated new patient data. A switchover of the ventilating apparatus to the new adjustment can occur by means of a control command.

Such a method wherein the ventilating apparatus and the patient are simulated makes possible an estimate of the new patient data as a consequence of the new adjustment without the occurrence of any effect on the patient who continues to be ventilated according to the original adjustment. If the new adjustment proves to be advantageous in that patient data is obtained as expected values that are more optimal with respect to the original setting, then a switchover of the ventilating apparatus to the new adjustment can take place by means of a control command such as by means of a manually actuable switch. After the simulation of the new adjustment, it is also possible to manually adjust the ventilating apparatus to the new ventilating data as usual.

An important improvement can, if required, be obtained in that the patient data continue to be applied to the second simulator unit (patient model) and that the parameters for the patient model and thereby for the simulation are improved from these patient data. In this way, a reaction behavior of the patient can be introduced in a certain manner into the patient model corresponding to the patient and, by continued improvement, the estimate of the effects for a simulated new adjustment of the ventilating apparatus becomes more reliable.

BRIEF DESCRIPTION OF THE DRAWING

The invention will now be described with reference to the single FIGURE which shows a schematic block diagram of an arrangement for carrying out the method of the invention.

DESCRIPTION OF THE PREFERRED EMBODIMENTS OF THE INVENTION

The method of the invention proceeds from the ventilating apparatus disclosed, for example, in U.S. Pat. No. 4,211,221 incorporated herein by reference.

This ventilating apparatus 2 ventilates a patient and the measured values taken up via patient sensors 3 are displayed as actual patient data 11 with a first display unit 1. The measured values sensed at the patient with known measuring devices are, for example, breathing pressure, breathing flow and, if required, also values of the blood gas concentrations. This known basic unit is now changed in such a manner that an adjusting unit 5 separate from the ventilating apparatus 2 is provided which permits the ventilating apparatus to be shifted or adjusted with respect to its adjusting values 9 such as breathing volume, frequency and the like. The adjusting unit 5 is separated from the ventilating apparatus 2 by means of a control switch 4 which, when closed delivers the control command for accepting the adjusted values from the adjusting unit 5 into the ventilating apparatus 2.

When the switch 4 is opened, the adjusting values desired or selected by the user do not immediately reach the ventilating apparatus 2; instead, they reach a first simulator unit 6 simulating the characteristic values of the ventilating apparatus. This simulator unit 6 generates a fictitious output signal which acts on the second simulator unit 7 simulating the patient. This simulator unit 7 can, for example, be a lung model with the parameters of resistance and compliance. The fictitious output values in this case are pressure and flow. The patient model then supplies the simulated measurement values 10 as output variables which are displayed to the user as simulated follow-up values by means of a second display unit 8.

With an opened control switch 4, the user can change the adjustment at the adjustment unit 5 as desired without affecting the actual ventilation of the patient. The user can adjust to a desired fictitious patient value which approximates the therapeutic objective and can perform practical exercises and study the behavior of the simulated patient as well as the simulated ventilating apparatus. The advantage afforded is that the retention time of the patient, for example, in the intensive care unit, is significantly reduced so that erroneous adjustments are not first recognized after they have already had a damaging effect on the patient; instead, the erroneous adjustments are recognized in advance as a simulated erroneous step without a reaction in the patient.

The reliability of the simulation is dependent upon the quality of the model, that is, of the model of the ventilating device and of the patient. The first simulator unit 6 simulates a technical apparatus and this simulation is therefore simpler to realize. It must, however, be considered that the second simulator unit 7, that is the patient model, can also have reactions on the first simulator unit 6. For example, for the application of a specific tidal volume, a pressure limitation becomes operative in dependence upon the lung characteristic which can prevent the metering of the desired tidal volume.

As a rule, such characteristics can, however, be obtained from the technical description of the ventilating apparatus so that an active operational connection between the ventilating apparatus 2 and the first simulator unit 6 is not necessary.

In contrast, the second simulator unit 7 for the patient behavior performs differently. Here it is possible to describe the actual patient behavior from the patient data which are sensed as measured values 11. The parameters for the patient model can then be obtained by means of a suitable identification method and they can be estimated with respect to their magnitude and trend. For example, it is possible to determine the lung characteristics of resistance and compliance from the course of the pressure and flow of the breathing gas taken up so that a linear lung model can be used for the second simulator unit 7.

If the user is in agreement with the resulting fictitious values generated by the simulator units, then the new adjusting values can be transmitted to the ventilating apparatus by closing the control switch 4 and the actual effect of the adjustment on the patient can be observed from the first display unit 1. If both displays 1 and 2 are looked at simultaneously or even in a suitable format one above the other on the same screen, the operator can immediately draw conclusions as to the quality of the simulation.

In contrast to the known simulators such as flying simulators, the user can check the possible effects of the adjusted changes immediately in the ventilating process which proceeds in a routine manner without the adjusted changes first having been made with effects on the patient.

It is understood that the foregoing description is that of the preferred embodiments of the invention and that various changes and modifications may be made thereto without departing from the spirit and scope of the invention as defined in the appended claims.

What is claimed is:

1. A method of controlling a ventilating apparatus for which a new adjustment selected according to patient data is to be made for optimization after a work-in time period, the method comprising the steps of:

connecting both a first simulator unit defining a model of the ventilating apparatus and simulating the characteristic values of the ventilating apparatus and a second simulator unit defining a model of the patient and simulating the patient parameters derived from the patient data to said ventilating apparatus such that the new adjustment is first carried out on said first simulating unit without changing the adjustment of said ventilating apparatus thereby obtaining resulting output values at the output of said first simulator unit;

coupling said resulting output values of said first simulator unit with said patient data of said second simulator unit such that effects of the new adjustment on the patient can be derived as simulated new patient data; and, switching over said ventilating apparatus to said new adjustment via a control command.

2. The method of claim 1, wherein the application of the patient data to said second simulator unit is continued; and, the parameters for said patient module are improved from this patient data thereby improving the simulation.

3. A circuit arrangement for carrying out a method of controlling a ventilating apparatus for which a new adjustment selected according to patient data is made for optimization after a work-in time period, the circuit arrangement comprising:

a plurality of sensors for sensing respective data on the patient;

a first display unit for receiving said data;

a first simulator unit defining a model of the ventilating apparatus and simulating the characteristic values thereof;

a second simulator unit connected to said sensors for also receiving said data, said second simulator unit defining a model of the patient and simulating the patient parameters derived from the patient data;

adjusting means for setting said new adjustment, said adjusting means being connected to said first simulator unit so as to permit said new adjustment to be carried out in said first simulator unit and to provide output values indicative thereof while the adjustment of said ventilating apparatus remains unchanged;

said second simulator unit having an input connected to said first simulator unit for receiving said output values thereof and coupling said output values with the patient data so as to facilitate the derivation of the effect of the new adjustment on the patient as simulated new patient data;

a second display unit connected to said second simulator unit for receiving and displaying the simulated new patient data; and, a control switch for selectively connecting said adjusting means to the ventilating apparatus in response to a control command for setting the ventilating apparatus to said new adjustment.

* * * * *